(12) United States Patent
Matsuda et al.

(10) Patent No.: US 7,718,556 B2
(45) Date of Patent: *May 18, 2010

(54) MEDICAL FILM

(75) Inventors: Shojiro Matsuda, Ayabe (JP); Hitoshi Ohtani, Ayabe (JP); Yoshimi Tanaka, Ayabe (JP); Hideki Tadokoro, Hiroshima (JP)

(73) Assignees: Gunze Limited, Kyoto (JP); JMS Co., Ltd., Hiroshima (JP)

( * ) Notice: Subject to any disclaimer, the term of this patent is extended or adjusted under 35 U.S.C. 154(b) by 52 days.

This patent is subject to a terminal disclaimer.

(21) Appl. No.: 10/536,590

(22) PCT Filed: Dec. 8, 2003

(86) PCT No.: PCT/JP03/15687

§ 371 (c)(1),
(2), (4) Date: May 26, 2005

(87) PCT Pub. No.: WO2004/054635

PCT Pub. Date: Jul. 1, 2004

(65) Prior Publication Data

US 2006/0094318 A1 May 4, 2006

(30) Foreign Application Priority Data

Dec. 16, 2002 (JP) .............................. 2002-364348

(51) Int. Cl.
*A61F 2/02* (2006.01)
*A61F 2/06* (2006.01)
*B32B 5/04* (2006.01)
*B32B 27/04* (2006.01)
*B32B 27/12* (2006.01)

(52) U.S. Cl. ........................ 442/123; 442/118; 442/164; 442/312; 424/402; 606/228; 606/230; 623/1.45; 623/1.5; 623/23.75

(58) Field of Classification Search ................ 606/228, 606/230, 231; 442/123, 181, 304, 327; 424/426, 424/444

See application file for complete search history.

(56) References Cited

U.S. PATENT DOCUMENTS 4,374,063 A * 2/1983 Consolazio et al. ......... 530/355

(Continued)

FOREIGN PATENT DOCUMENTS

EP 0 734 736 10/1996

(Continued)

OTHER PUBLICATIONS

Japanese Office Action issued in Japanese Application No. 2003-406296, mailed Dec. 3, 2009 with a partial English Translation—4 pages.

*Primary Examiner*—Jennifer A Chriss
(74) *Attorney, Agent, or Firm*—Hamre, Schumann, Mueller & Larson, P.C.

(57) ABSTRACT

A medical film that is excellent in biocompatibility and bioabsorbability and has an excellent strength in suturing and bonding is provided. A reinforcing material 12 made of a biodegradable polymer is placed in a gelatin solution so as to allow the solution to infiltrate in the reinforcing material 12 and then the gelatin is dried. This allows the gelatin that has infiltrated entirely in an internal part of the reinforcing material 12 to gel, thereby forming a gelatin film 11. Thus, a medical film 1 in which the reinforcing material 12 and the gelatin film 11 are integrated is obtained. The gelatin film 11 preferably is a cross-linked gelatin film.

22 Claims, 7 Drawing Sheets

U.S. PATENT DOCUMENTS

| | | | |
|---|---|---|---|
| 5,447,940 A * | 9/1995 | Harvey et al. | 514/310 |
| 5,795,584 A | 8/1998 | Totakura et al. | |
| 5,854,381 A * | 12/1998 | Jurgens et al. | 528/354 |
| 6,599,323 B2 * | 7/2003 | Melican et al. | 623/23.72 |
| 2001/0016205 A1 | 8/2001 | Shimizu | |
| 2004/0137179 A1 | 7/2004 | Matsuda et al. | |

FOREIGN PATENT DOCUMENTS

| | | | |
|---|---|---|---|
| EP | 0 745 394 A2 | | 12/1996 |
| EP | 1 022 031 A1 | | 7/2000 |
| EP | 1 084 686 | | 3/2001 |
| EP | 1 098 024 | | 5/2001 |
| EP | 1 201 202 | | 5/2002 |
| JP | 6-254148 | | 9/1994 |
| JP | 8-317968 A | | 12/1996 |
| JP | 10/113384 | | 5/1998 |
| JP | 63-160845 | | 10/1998 |
| JP | 11/239610 A | | 9/1999 |
| JP | 2000-37450 A | | 2/2000 |
| JP | 2000-60956 | | 2/2000 |
| JP | 2000-197693 | | 7/2000 |
| JP | 2004-65780 | | 3/2004 |
| WO | WO 97/07833 | * | 3/1997 |
| WO | 98/22157 | | 5/1998 |
| WO | 99/63908 | | 12/1999 |
| WO | WO 02078568 A1 | * | 10/2002 |

* cited by examiner

MEDICAL FILM

TECHNICAL FIELD

The present invention relates to a medical film. In particular, the present invention relates to an antiadhesive material for preventing tissues in a living body from adhering to each other, a tissue prosthetic material for prosthetic restoration of a missing part of a tissue, or a graft cell-culturing sheet material for implanting a sheet-like tissue in a living body, which are excellent in biocompatibility and bioabsorbability and have an excellent strength in suturing.

BACKGROUND ART

In various clinical fields including cardiac surgery, orthopedics, neurosurgery, abdominal surgery, and obstetrics and gynecology, it has been a serious problem that after a surgical operation of various types or due to an external injury, tissues in an affected part in a living body adhere to one another. The adhesion of tissues, for instance, can cause pain or impair function, which, if serious, requires another surgical operation for separating the adhering tissues. Moreover, the adhesion also causes a problem of making a follow-up operation with respect to the primary disease difficult. To cope with these problems, conventionally, antiadhesive materials for covering and protecting tissues potentially subject to adhesion have been developed, for the purpose of preventing adhesion of tissues in a living body. A regenerated oxidized cellulose fabric, a hyaluronic acid-carboxymethyl cellulose mixture film, etc., have been in actual use as antiadhesive materials.

More specifically, in order for such an antiadhesive material to perform the antiadhesive function, it is necessary for the antiadhesive material to be present at an application site (affected part) at which adhesion possibly occurs during a required period of time so as to function as a barrier between tissues at the application site, be decomposed finally, and be absorbed in the body. In other words, the antiadhesive material is required to be excellent in biocompatibility, bioabsorbability, and the like.

Even in the case of such an antiadhesive material excellent in biocompatibility and the like as described above, it has to be fixed firmly at the application site so as to perform these functions sufficiently. As a fixing method for this purpose, normally, methods of suturing with a suture thread, bonding with an adhesive, and the like have been used.

However, the conventional antiadhesive material as described above has difficulty in, for instance, performing the antiadhesive function while maintaining its form in a living body for a required period of time, and since it does not have a strength sufficient for durability in suturing, bonding, or the like, it is torn in some cases. Thus, the handling of the antiadhesive material and the fixing of the same at an application site are difficult.

For instance, antiadhesive materials formed with gelatin films excellent in biocompatibility, bioabsorbability, etc., which recently have been studied and developed, and now are in actual use (see JP 11(1999)-239610 A and JP 2000-37450 A, for instance) are inferior in allowing themselves to adhere and fix to surfaces of tissues at an application site. Therefore, for fixing the same at an application site, the suturing and/or bonding methods as described above are used. However, such gelatin films, when applied to tissues, absorb moisture of the tissues and become in a hydrogel state containing water. Therefore, they have a problem of being difficult to fix by suturing, etc.

DISCLOSURE OF INVENTION

Therefore, it is an object of the present invention to provide a medical film that is, for example, excellent in biocompatibility and bioabsorbability and has an excellent strength in suturing and bonding.

In order to achieve the above object, the present invention provides a medical film including a gelatin film, wherein a reinforcing material that is made of a biodegradable polymer further is provided, the reinforcing material is disposed so as to extend over an entire area in a plane direction of at least one of a surface and an internal part of the gelatin film, and the reinforcing material and the gelatin film are integrated with each other. It should be noted that in the present invention, the gelatin film may be, for instance, porous or nonporous.

In the medical film of the present invention, a sufficient strength is imparted by disposing the reinforcing material made of a biodegradable polymer so as to extend over an entire area in a plane direction of at least one of a surface and an internal part of the gelatin film and integrating the reinforcing material with the gelatin film. Therefore, for example, the medical film is easy to fix at an application site, and the fixed state can be maintained during a required period. Accordingly, when the medical film of the present invention is used as, for instance, an antiadhesive material, the adhesion prevention effect due to the gelatin film can be performed sufficiently at the application site. Moreover, since the gelatin film is reinforced in its entirety, there is an advantage that, for example, the gelatin film can be used after being cut into a desired form or a size, so that the application site is not limited. Moreover, for example, even in the case where the medical film that has been fixed at the application site by suturing needs to be peeled off, suturing can be carried out as many times as needed at a portion of the medical film different from the portion that has already been subjected to suturing, because the medical film is reinforced in its entirety. Further, since the reinforcing material is made of a biodegradable polymer with biocompatibility that is field-proven in the clinical medicine, a problem that it remains in a living body and causes a foreign body reaction with tissues, for instance, can be avoided. Therefore, the medical film of the present invention can serve as, for example, an antiadhesive material that is particularly advantageous in the clinical field such as surgical operations.

It should be noted that the medical film of the present invention is not only applicable as an antiadhesive material described above, but also is useful as a tissue prosthetic material, an induction tube for a nerve, a sheet material for culturing a graft cell, a membrane for induction and regeneration of a tissue, or the like, for example.

BRIEF DESCRIPTION OF DRAWINGS

FIG. 10 shows photographs of reinforcing materials used in another example of the present invention, in which

BEST MODE FOR CARRYING OUT THE INVENTION

The shape of the medical film of the present invention is not limited particularly, and apart from the sheet form, it may be in a cylindrical form.

In the medical film of the present invention, the reinforcing material preferably is a fabric body or a film body, and the film form may be, for instance, a porous film or a non-porous film.

The medical film of the present invention may be in the form of a laminate in which the reinforcing material is laminated on at least one film surface of the gelatin film so that the reinforcing material extends over an entire area of the film surface, for example. In this case, a means for arranging the reinforcing material on the gelatin film is not limited particularly. They may be integrated, for instance, by using an adhesive or the like, or alternatively, they may be integrated due to the gelling of the gelatin that has infiltrated at least partially in an internal part of the reinforcing material. Thus, by gelling the gelatin in the internal part of the reinforcing material, it is possible to carry out the formation of the gelatin into a film form and the integration concurrently, for example. Additionally, the manufacture is facilitated further since a specific step for integrating the gelatin film with the reinforcing material by using another means such as an adhesive is unnecessary, and they are integrated firmly.

The form of the medical film of the present invention is not limited to that described above. For instance, on at lease one film surface of the gelatin film, a part or an entirety of the reinforcing material may be inside the gelatin film, and the reinforcing material and the gelatin film may be integrated due to the gelling of the gelatin that has infiltrated partially or entirely in the reinforcing material. Alternatively, the reinforcing material may be embedded in the gelatin film entirely, and the reinforcing material and the gelatin film may be integrated due to the gelling of the gelatin that has infiltrated entirely in the reinforcing material.

In the medical film of the present invention, the foregoing fabric body as the reinforcing material is not limited particularly, but it preferably is a nonwoven fabric, a woven fabric, a knitted fabric, or a braid, more preferably, at least one complex selected from the group consisting of a complex of a nonwoven fabric and a woven fabric, a complex of a nonwoven fabric and a knitted fabric, and a complex of a nonwoven fabric and a braid.

When the fabric body is a woven fabric or a knitted fabric, the thickness of a yarn is not limited particularly, and may be, for example, in a range of 10 to 500 d (11.1 decitex to 555.6 decitex), preferably in a range of 20 to 300 d (22.2 decitex to 333.3 decitex), particularly preferably in a range of 30 to 200 d (33.3 decitex to 222.2 decitex). Examples of the yarn include a multifilament yarn and a monofilament yarn, and among these, a multifilament yarn is preferable.

Figure 7:
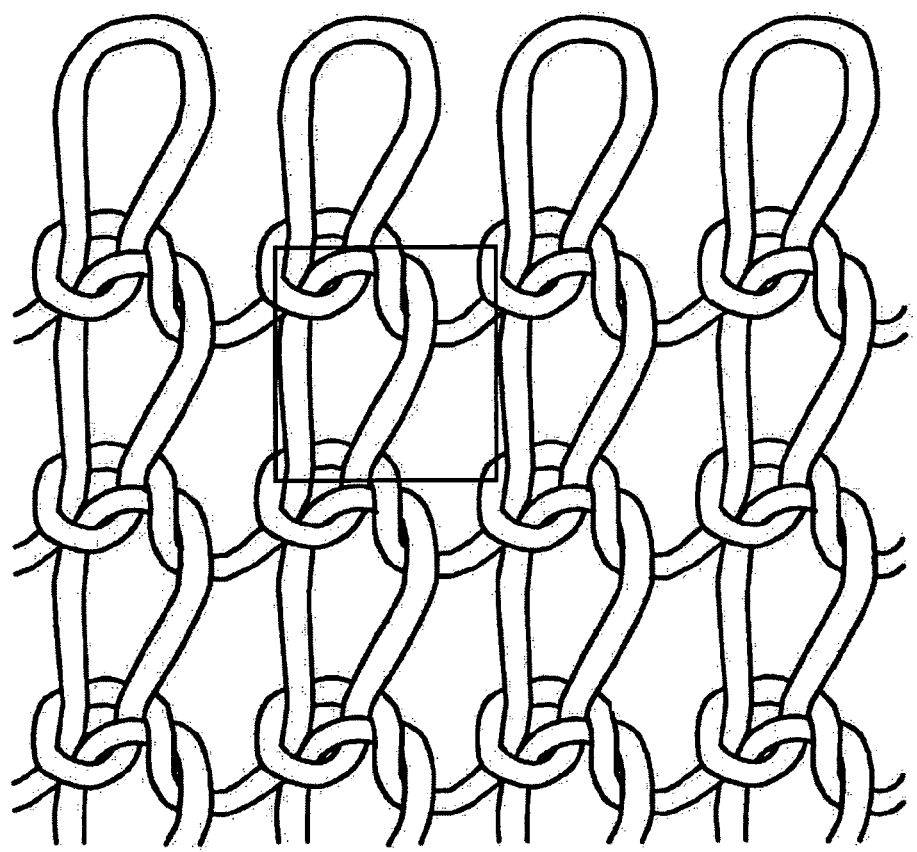
FIG. 7 is a diagram schematically illustrating a twin loop knit used in still another example of a medical film of the present invention.

When the fabric body is a knitted fabric such as a twin knit fabric, for example, a unit of stitches (also referred to as a "repeated loop") thereof has, for example, a vertical length of 0.1 mm to 10 mm and a horizontal length of 0.1 mm to 10 mm, preferably a vertical length of 0.3 to 8 mm and a horizontal length of 0.3 mm to 8 mm, more preferably a vertical length of 0.5 mm to 6 mm and a horizontal length of 0.5 mm to 6 mm. It should be noted that the unit of stitches refers to, for example, in the twin knit fabric shown in the schematic view of FIG. 7, a portion surrounded by the rectangular frame. The length of the frame corresponds to "the vertical length of the unit", and the width of the frame corresponds to "the horizontal length of the unit".

In the case where the knitted fabric is a warp knitted fabric, a unit of stitches thereof has, for example, a vertical length of 0.1 mm to 10 mm and a horizontal length of 0.1 mm to 10 mm, preferably a vertical length of 0.3 to 8 mm and a horizontal length of 0.3 mm to 8 mm, more preferably a vertical length of 0.5 mm to 6 mm and a horizontal length of 0.5 mm to 6 mm. It should be noted that the unit of stitches of the warp knitted fabric refers to a diamond-shaped portion shown in, for example, photographs of FIGS. 10B and 10C, which will be described later. The length of the diamond-shaped portion in the vertical direction corresponds to "the vertical length of the unit", and the length of the diamond-shaped portion in the horizontal direction corresponds to "the horizontal length of the unit". The warp knitted fabric may be in the form of "a mesh with diamond-shaped pores" as shown in the below-mentioned FIG. 10B or "a mesh with hexagon pores" as shown in the below-mentioned FIG. 10C. It should be noted that, for example, "Knitted Fabric Handbook" (revised edition, published by Japan Textile Laboratory in November 1968) discloses various forms of warp knitted fabric, typified by a mesh with diamond-shaped pores and a mesh with hexagon pores.

The foregoing nonwoven fabric preferably is a nonwoven fabric manufactured by, for instance, melt blowing, needle punching, spunbonding, flash spinning, or the like.

In the medical film of the present invention, the foregoing reinforcing material preferably is processed by hot pressing. The hot pressing improves the binding of fibers forming the reinforcing material and prevents fuzzing, for example.

The property and shape of the foregoing reinforcing material are not limited particularly, but the reinforcing material preferably has a density in a range of 5 g/m$^2$ to 200 g/m$^2$ and a thickness in a range of 10 μm to 500 μm since a sufficient strength is obtained.

The reinforcing material preferably has a yarn threading tension in a range of 0.3 N to 200 N. The yarn threading tension is determined by, for instance, the following method.

(Method for Measuring the Yarn Threading Tension)

A sample (10 mm×30 mm) is prepared, and ends of the sample in its lengthwise direction are fixed so that a distance between two chucks is 20 mm. Next, a 3-0 nylon suture with needle (Nesco Suture, ½ circle round-bodied needle) (trade name: Nesco Suture, manufactured by AZWELL Inc.) is threaded through the sample at a midpoint in the lengthwise direction and 2 mm from an edge in its width direction, and ends of the suture are fixed at a distance of 50 mm from the point at which the suture is threaded. Then, with the sample being maintained in the fixed state, the ends of the suture are pulled at a rate of 100 mm/min, and a maximal force (yarn threading tension: a unit thereof is "N") is measured using a measuring device (trade name: Instron 4302, manufactured by Instron Corporation).

In the medical film of the present invention, the film body as the reinforcing material is not limited particularly, and a film body manufactured by a normal known method such as pressing, casting, extruding, or the like may be used as the foregoing film body. The film body preferably has a thickness, for instance, in the same range as that of the fabric body. Other than the film body, a sponge body also can be used as the reinforcing material.

In the medical film of the present invention, the biodegradable polymer preferably is at least one polymer selected from the group consisting of polylactic acid, lactic acid-caprolactone copolymer, and polyglycolic acid. Among these, it preferably is polylactic acid and/or lactic acid-caprolactone copolymer since it exhibits an appropriate degradability and absorbability when it forms the reinforcing material.

In the medical film of the present invention, the foregoing reinforcing material preferably is treated so that hydrophilicity is imparted thereto. By imparting hydrophilicity to a surface of the reinforcing material, the reinforcing material exhibits a higher affinity to a gelatin solution or a gelatin film. This allows excellent integration of the reinforcing material with the gelatin film to be achieved, thereby hardly causing the reinforcing material to separate from the gelatin film. Examples of the method for imparting hydrophilicity include plasma treatment, glow discharge treatment, corona discharge treatment, ozone treatment, graft treatment, coating, chemical treatment, ultraviolet irradiation, etc. Among these, plasma treatment is preferable.

In the medical film of the present invention, the gelatin film preferably is a cross-linked film that is cross-linked so as to be, for instance, degraded in a living body after a desired period of time lapses. This is because, when the medical film is used as antiadhesive material, as described above, the medical film is required to be present at an application site during a required period of time and perform an antiadhesive function, and after the period lapses, it is required to be degraded and absorbed in the living body so that a foreign body reaction with tissues therein should be avoided. It should be noted that as the degree of cross-linkage of the gelatin film is relatively higher, it indicates that the degradation of the same in a living body is slower.

In the medical film of the present invention, the gelatin film preferably is cross-linked by at least one method selected from ultraviolet treatment, heat treatment, chemical cross-linking agent treatment, and other means.

In the medical film of the present invention, the gelatin film preferably is cross-linked under conditions of an ultraviolet lamp of 4 W to 40 W, an irradiation time of 0.1 hour to 100 hours, and an irradiation distance of 5 cm to 100 cm. The ultraviolet irradiation preferably is carried out under conditions of, for instance, an ultraviolet intensity of 0.05 mW/cm$^2$ to 50 mW/cm$^2$ and an ultraviolet dose of 1 J/cm$^2$ to 100 J/Cm$^2$, more preferably an ultraviolet intensity of 0.5 mW/cm$^2$ to 10 mW/cm$^2$ and an ultraviolet dose of 5 J/Cm$^2$ to 100 J/cm$^2$. The ultraviolet intensity can be set, for example, by setting a wattage of an ultraviolet lamp and a distance between the ultraviolet lamp and an object to be irradiated (i.e., the gelatin film), and the ultraviolet dose is represented by a product of an ultraviolet intensity and an irradiation time and thus can be set by setting the ultraviolet intensity and the irradiation time. It should be noted that the ultraviolet irradiation exhibits a degree of cross-linkage that varies depending on various conditions, for instance, the ultraviolet intensity, that is, the power of the ultraviolet lamp, the irradiation distance, etc. Therefore, the foregoing conditions may be determined appropriately according to a desired degradation time of the gelatin film. The ultraviolet irradiation may be carried out with a plurality of ultraviolet lamps arranged in parallel, for example.

In the medical film of the present invention, a time of presence of the gelatin film in a living body preferably is in a range of 12 hours to 30 days. In the present invention, the "time of presence in a living body" refers to a time that lapses from the application of the medical film as an antiadhesive material in a living body until the degradation and absorption of the gelatin film in the living body (hereinafter it also is referred to as a "degradation time"). It should be noted that even the same gelatin film exhibits a different time of presence in a living body depending on the organ to which the gelatin film is applied. Therefore, the time of presence in a living body preferably is set according to the application site.

In the medical film of the present invention, the gelatin film preferably has a thickness in a range of 20 μm to 2000 μm from the viewpoint of handleability.

Since the medical film of the present invention is applied in a living body, a concentration of endotoxin contained in the gelatin preferably is more than 0 and not more than 200 EU/g, more preferably, not more than the detection limit, so that the safety is secured. It should be noted that ideally no endotoxin is contained, that is, the content of endotoxin is zero, but this is not practical. Therefore, the lower limit thereof is described to be "more than 0". Further, it is preferable that the medical film of the present invention substantially does not contain other toxic substances, or that contents of the same are within legally or medically tolerable ranges.

Though the degradation time of the gelatin film varies with the application site, as described above, the gelatin film of the present invention preferably is degraded in, for instance, 12 hours to 90 days, more preferably in a range of 1 day to 60 days, particularly preferably in a range of 2 days to 30 days. In the case where the degradation time is not less than 12 hours, it is possible to prevent the adhesion of tissues sufficiently, and in the case where the degradation time is not more than 90 days, particularly not more than 30 days, it is possible to prevent adhesion sufficiently, while the gelatin film does not cause a reaction other than the adhesion prevention (for instance, the foreign body reaction, etc.) at the application site. The degradation time may be set by a cross-linking treatment that will be described later.

The thickness of the gelatin film can be determined appropriately according to, for instance, the application site, the desired degradation time of the gelatin film, etc., and it is, for instance, in a range of 20 μm to 2000 μm, preferably in a range of 30 μm to 500 μm, more preferably in a range of 50 μm to 300 μm. The thickness of the gelatin film of, for instance, not less than 20 μm leads to a further improved strength, and the thickness thereof of not more than 2000 μm leads to a further improved flexibility, thereby making the gelatin film easy to handle.

The foregoing gelatin film has a water content measured by a method described below of, for instance, 70% to 99%, preferably 75% to 97.5%, more preferably 80% to 95%. It should be noted that the water content indicates that, for instance, as it is relatively lower, the degradation of the gelatin film in a living body is slower. In the case where the gelatin film is obtained by cross-linking, the water content indicates that as it is relatively lower, the degree of cross-linkage is higher and the degradation of the same in a living body is slower.

The water content is measured in the following manner, for instance. First, the film is immersed in water at 25° C. for 12 hours, and thereafter, the wet weight thereof is measured. Subsequently, the film is dried completely with a vacuum dryer, and the dry weight of the film thus dried is measured. Then, the water content is calculated by substituting the foregoing weights in an equation shown below:

$$\text{water content (\%)}=100\times[(\text{wet weight}-\text{dry weight})/(\text{wet weight})]$$

Examples of a material for the gelatin film include, for instance, gelatins extracted from bones, tendons, skins, combs, etc. of mammals and bird species such as cow, pig, horse, fowl, etc. Such a gelatin may be prepared by, for instance, extracting from the foregoing animals, but normally, a commercially available product can be used. A method for the extraction is not limited particularly, and examples of the same include conventionally known acid treatment, alkali treatment, etc.

As the commercially available gelatin, for instance, an alkali-treated gelatin is preferable that contains only a very small amount of endotoxin and that is therefore excellent in safety. More specifically, examples of the same include a cow-origin alkali-treated gelatin, a pig-origin acid-treated gelatin, and a pig-origin alkali-treated gelatin manufactured by Nippi Inc., and the like.

Further, as materials for the gelatin film, apart from gelatin, additives may be used. Examples of the additives include glycerin, polyethylene glycol, and hyaluronic acid for imparting flexibility to the film, as well as antimicrobial agents, anti-inflammatory agents, etc.

The gelatin film can be manufactured by forming gelatin in a film form by, for instance, casting, extruding, or another method, among which casting is used preferably.

The film formation by casting can be carried out by, for instance, the following manner.

First, gelatin as a material is dissolved in a solvent in a heated state. As the solvent, for instance, distilled water, dimethyl sulfoxide (DMSO), etc., and mixture solutions of these can be used. Among these, distilled water is preferable from the viewpoint of handlability. The proportion of gelatin added per 100 ml of a solvent is, for instance, in a range of 0.1 g to 50 g, preferably in a range of 1 g to 30 g, more preferably in a range of 3 g to 20 g. The temperature for dissolution is, for instance, in a range of 10° C. to 80° C., preferably in a range of 30° C. to 70° C., more preferably in a range of 40° C. to 60° C. Further, the dissolution time is not limited particularly as long as the gelatin is dissolved, and for instance, it is in a range of 1 minute to 100 hours, preferably in a range of 5 minutes to 50 hours, more preferably in a range of 10 minutes to 24 hours.

In the case where additives other than gelatin as mentioned above are contained, the proportion of the additives added per 1 g of gelatin is, for instance, in a range of 1 mg to 20 g, preferably in a range of 5 mg to 10 g, more preferably in a range of 10 mg to 5 g.

Such a gelatin solution is cast in a petri dish, and is dried, whereby a gelatin film is produced. The size of the petri dish is not limited particularly, and may be set according to desired length, width, thickness, etc. of a film, or alternatively, after forming a film, the film may be cut into a desired size before use.

The gelatin solution preferably is cast, for instance, in a range of 0.01 ml to 5 ml per unit area (cm$^2$) of a petri dish, more preferably in a range of 0.03 ml to 3 ml, particularly preferably in a range of 0.05 ml to 1 ml.

The drying can be carried out, for instance, under a condition of natural drying, heat drying, reduced-pressure drying (vacuum drying), forced exhaust drying, forced-circulated convection, or the like. More specifically, a drying temperature is, for instance, in a range of −40° C. to 90° C., preferably in a range of 0° C. to 50° C., more preferably in a range of 10° C. to 30° C. A drying time is, for instance, in a range of 1 hour to 200 hours, preferably in a range of 3 hours to 100 hours, more preferably in a range of 5 hours to 48 hours.

The foregoing series of film forming steps preferably is carried out aseptically, for instance, on a clean bench, or in a clean room. This is intended to prevent the gelatin film from being contaminated by various germs breeding during the steps. Therefore, it is preferable to use manufacturing equipment sterilized, for instance, by using an autoclave, by using ethylene oxide gas (EOG), by hot-air sterilization, by applying electron beams, etc. Further, the gelatin solution also preferably is subjected to the foregoing steps after it is sterilized by, for instance, conventional known filtering sterilization.

The gelatin film thus obtained may be used as it is, but it preferably is cross-linked further, since by so doing the degradation time thereof in a living body can be set desirably, as described above.

Examples of an applicable cross-linking method include ultraviolet (UV) irradiation, heat treatment, treatment using a chemical cross-linking agent, etc. Examples of the chemical cross-linking agent include aldehydes, epoxies, carbodiimides, isocyanates, tannin, chromium, etc. Examples of aldehyde include formaldehyde, glutaraldehyde, acid aldehyde, glyoxal, dialdehyde malonate, dialdehyde succinate, aldehyde phthalate, dialdehyde starch, polyacrolein, polymethacrolein, etc. Examples of epoxy include glycerol diglycidyl ether, sorbitol diglycidyl ether, ethylene glycol diglycidyl ether, polyethylene glycol diglycidyl ether, polyglycerol polyglycidyl ether, etc. Examples of carbodiimide include water-soluble carbodiimides (for instance, 1-ethyl-3-(3-dimethylaminopropyl)carbodiimide, cyclohexyl-3-(2-morpholinoethyl)carbodiimide, etc.), dicyclohexyl carbodiimide, etc. The type of the chemical cross-linking agent used is not limited particularly as long as the gelatin is cross-linked, and, for instance, one type may be used alone, or two or more types may be used in combination.

Among the foregoing cross-linking methods, UV irradiation, heat treatment, or using UV irradiation and heat treatment in combination is preferable. UV irradiation and/or heat treatment makes it possible to achieve easily a cross-linked gelatin film that has more excellent effects such as being degradable in a living body in a relatively short time, leaving no toxic chemical substance of a low molecular weight, and hardly causing deformation of a product.

In the case where the cross-linking is carried out by UV irradiation, conditions of, for instance, a power of an UV lamp, an irradiation time, an irradiation distance, etc. can be set appropriately according to a desired degradation time of the gelatin film. The power of an UV lamp is, for instance, in a range of 4 W to 40 W, preferably in a range of 8 W to 30 W, more preferably in a range of 12 W to 20 W. The irradiation time is, for instance, in a range of 0.1 hour to 100 hours, preferably in a range of 0.5 hour to 60 hours, more preferably in a range of 1 hour to 50 hours. The irradiation distance is, for instance, in a range of 1 cm to 100 cm, preferably in a range of 5 cm to 90 cm, more preferably in a range of 10 cm to 80 cm.

More specifically, for instance, in the case where the power of a UV lamp is in a range of 4 W to 40 W, the irradiation time and the irradiation distance preferably are in a range of 0.1 hour to 100 hours and in a range of 1 cm to 100 cm, respectively. More preferably, in the case where the power of a UV lamp is in a range of 8 W to 30 W, the irradiation time and the irradiation distance are in a range of 0.5 hour to 60 hours and in a range of 5 cm to 90 cm, respectively. Particularly preferably, in the case where the power of an UV lamp is in a range of 12 W to 20 W, the irradiation time and the irradiation distance are in a range of 1 hour to 50 hours and in a range of 10 cm to 80 cm, respectively. By carrying out the ultraviolet irradiation with a plurality of ultraviolet lamps arranged in parallel, the gelatin film can be treated more uniformly within a short time.

Particularly, a cross-linked gelatin film prepared under conditions of the power of an UV lamp of 15 W, the irradiation time of 5 hours to 30 hours, and the irradiation distance of 30 cm to 70 cm was proven to be more excellent in degradability, safety, strength, etc. by experiments conducted by the inventors. More specifically, for instance, a cross-linked gelatin film with a thickness of 100 μm that was cross-linked under conditions of the power of an UV lamp of 15 W, the irradiation time of 20 hours, and the irradiation distance of 60 cm degraded and disappeared in about one week in the case where it was sutured in an abdominal cavity of a rat, and in about four weeks in the case where it was sutured to a pericardial sac of a dog. This proves that the cross-linked gelatin films prepared under the foregoing conditions so as to have desired degradation times according to a variety of application sites have excellent utility, particularly in the clinical medicine.

On the other hand, the heat treatment preferably is carried out under vacuum at a temperature of 60° C. to 180° C. for 5 minutes to 72 hours, for example.

Next, since the reinforcing material of the present invention is intended for reinforcing the gelatin film especially during an operation or until the gelatin film is absorbed during the use of the medical film, it need not remain in a body after the gelatin film performs its function and is degraded and absorbed, and in order that the reinforcing material should be prevented from remaining in a body and causing an unnecessary foreign body reaction with tissues at an application site, it is necessary that the reinforcing material should be degraded and absorbed. For this purpose, a fabric body, a film body, or the like made of a biodegradable polymer as described above is used.

It should be noted that the reinforcing material may be composed of a single layer, or a laminate including two or more layers. In the case where it is a laminate, it may be composed of fabric bodies or film bodies of one kind, or alternatively, it may be composed of fabric bodies or film bodies of two or more kinds, for instance.

The reinforcing material is not limited particularly as long as it does not remain in a living body as described above, but since it is used for a reinforcing purpose, it desirably has some strength and flexibility, and additionally, degradability. Further, it preferably has biocompatibility based on usage in the clinical medicine, and causes few foreign body reactions and inflammations. Therefore, examples of the foregoing biodegradable polymer include, as described above, polylactic acid, lactic acid-caprolactone copolymer, polyglycolic acid, lactic acid-glycolic acid copolymer, lactic acid-ethylene glycol copolymer, polydioxanon, glycolic acid-caprolactone copolymer, glycolic acid-trimethylene carbonate copolymer, glycolic acid-dioxanon-trimethylene carbonate copolymer, collagen, chitin, chitosan, fibrin, etc. Preferably, polylactic acid, lactic acid-caprolactone copolymer, polyglycolic acid, or collagen is used.

Examples of the form of the foregoing fabric body include a woven fabric, a nonwoven fabric, a knitted fabric, a braid such as flat braid, etc., as described above. Among these, a nonwoven fabric is preferable since it has a structure in which fine fibers tangle with one another highly, and hence, it does not have an orientation, allows the thickness to be set easily, and provides excellent flexibility. A knitted fabric, such as a twin loop knit, and a woven fabric are particularly preferable since they are further excellent in ease of setting a thickness, flexibility, strength, and yarn threading tension. Furthermore, a material (a complex) obtained by integrating a nonwoven fabric with any one of a knitted fabric, a woven fabric, and a braid is particularly preferable since it has the foregoing advantages of the both together.

In the case where the reinforcing material is the fabric body described above, the yarn threading tension preferably is, for instance, in a range of 0.3 N to 200 N, more preferably in a range of 0.4 N to 150 N, particularly preferable in a range of 0.5 N to 100 N. It should be noted that this value can be determined by the above-described method.

The density of the fabric body is, for instance, in a range of 3 g/m$^2$ to 200 g/m$^2$ or 5 g/m$^2$ to 200 g/m$^2$. In another instance, the density of the fabric is in a range of 8 g/m$^2$ to 80 g/m$^2$. In yet another instance, the density of the fabric is in a range of 10 g/m$^2$ to 60 g/m$^2$.

The fabric body is determined appropriately according to the size and desired strength of the gelatin film, and has a thickness, for instance, in a range of 10 μm to 1000 μm, preferably in a range of 20 μm to 800 μm, more preferably in a range of 30 μm to 600 μm. Further, in the case where the fabric body is a laminate as described above, it preferably has a thickness, for instance, in a range of 10 μm to 1000 μm, more preferably in a range of 20 μm to 800 μm, particularly preferably in a range of 30 μm to 600 μm. It should be noted that this applies to the film body as a reinforcing material.

The nonwoven fabric can be prepared by, for instance, melt blowing, needle punching, spunbonding, or flash spinning as a conventionally known process, or the like. Among these, the melt blowing is particularly preferable since it does not require the use of a solvent, and manufactures a thin fabric easily by decreasing diameters of fibers and tangling thin fibers highly.

The melt blowing is a method for manufacturing a web of self-adhesive microfibers by, for instance, blowing a molten material from a die of an extruder onto an accumulating screen with high speed airflow so that pieces of the material thus blown cross and tangle.

In the case where a nonwoven fabric made of the polylactic acid or the polyglycolic acid is manufactured, a polymer obtained by polymerizing lactide or glycolide as a material is used. In the case where a nonwoven fabric made of the lactic acid-caprolactone copolymer is manufactured, a copolymer obtained by mixing and polymerizing lactide or caprolactone is used. In the latter case, a molar ratio (A:B) of lactide (A) and caprolactone (B) is, for instance, in a range of 85:15 to 40:60, preferably in a range of 82:18 to 42:58, more preferably in a range of 80:20 to 45:55.

The fabric body of the nonwoven fabric or the like thus prepared by the method as described above can be used as it is, as a reinforcing material in the medical film of the present invention, but it preferably is subjected further to hot pressing so that linting such as fuzzing is prevented as described above, and the binding of fibers is improved.

The hot pressing may be carried out, for instance, immediately after the formation of a web of a nonwoven fabric, or after the vacuum heat drying. It should be noted that the foregoing treatment preferably is applied to both sides of the reinforcing material such as the nonwoven fabric.

In the case where the hot pressing is carried out immediately after the formation of a web, it is carried out under conditions of, for instance, a temperature in a range of 65° C. to 95° C. and a pressure in a range of 0.01 MPa to 5 MPa, preferably a temperature in a range of 70° C. to 85° C. and a pressure in a range of 0.05 MPa to 2 MPa, more preferably a temperature in a range of 75° C. to 80° C. and a pressure in a range of 0.1 MPa to 1 MPa.

On the other hand, in the latter case, first, the vacuum heat drying is carried out, for instance, under the following conditions. A drying temperature is, for instance, in a range of 40° C. to 135° C., preferably in a range of 50° C. to 125° C., more preferably in a range of 60° C. to 115° C. Further, a drying time is, for instance, in a range of 1 hour to 70 hours, preferably in a range of 5 hours to 50 hours, more preferably in a range of 10 hours to 30 hours.

Subsequently, the hot pressing preferably is carried out under the following conditions. For instance, the conditions are, for instance, a temperature in a range of 80° C. to 110° C. and a pressure in a range of 0.01 MPa to 5 MPa, preferably a temperature in a range of 85° C. to 105° C. and a pressure in a range of 0.05 MPa to 2 MPa, more preferably a temperature in a range of 90° C. to 100° C. and a pressure in a range of 0.1 MPa to 1 MPa. If the heating temperature is not lower than 80° C., fuzzing can be eliminated sufficiently, while if the heating temperature is not higher than 110° C., excellent flexibility can be maintained.

Also in the case where the reinforcing material is, for instance, a two or more layers laminate composed of two or more fabric bodies as described above, the hot pressing may be applied after the fabric bodies are laminated so that the fabric bodies are integrated.

Further, the reinforcing material preferably is subjected to a hydrophilicity imparting treatment so that the adhesivity of the reinforcing material with the gelatin film is improved. Examples of the hydrophilicity imparting treatment include plasma treatment, glow discharge treatment, corona discharge treatment, ozone treatment, graft treatment, coating, chemical treatment, ultraviolet irradiation, etc., as described above. Among these, plasma treatment is preferable particularly.

Conditions for plasma treatment are not limited particularly, and the treatment preferably is carried out, for instance, in an oxygen atmosphere at a pressure of 1.33 Pa to 1330 Pa, at a temperature in a range of 0° C. to 100° C., with a power in a range of 5 W to 200 W, more preferably in an oxygen atmosphere at a pressure of 5 Pa to 500 Pa, at a temperature in a range of 10° C. to 50° C., with a power in a range of 10 W to 100 W. A treatment time may be, for instance, in a range of 1 second to 1000 seconds, preferably in a range of 3 seconds to 600 seconds.

In the foregoing plasma treatment, for instance, air, nitrogen, argon, helium, ammonia, carbon oxide, or water vapor may be used, apart from the foregoing oxygen gas.

The overall shape and size of the medical film of the present invention are not limited particularly and can be determined appropriately, for instance, according to an application site. For instance, it has an overall length in a range of 0.5 cm to 50 cm, an overall width of 0.3 cm to 20 cm, and an overall thickness of 20 μm to 2000 μm. Preferably, it has an overall length in a range of 0.7 cm to 30 cm, an overall width of 0.4 cm to 15 cm, and an overall thickness of 30 μm to 500 μm.

More preferably, it has an overall length in a range of 1 cm to 20 cm, an overall width of 0.5 cm to 10 cm, and an overall thickness of 50 μm to 200 μm.

The size of the reinforcing material is determined appropriately according to, for instance, an application site and a size of the gelatin film. The thickness of the reinforcing material preferably is in a range of 10 μm to 1000 μm, more preferably in a range of 20 μm to 800 μm, particularly preferably in a range of 30 μm to 600 μm.

Since the medical film includes the reinforcing material as described above, the yarn threading tension thereof preferably is, for instance, in a range of 0.20 N to 200 N, more preferably in a range of 0.25 N to 150 N, particularly preferably in a range of 0.30 N to 100 N.

As a method for arranging the reinforcing material on the cross-linked gelatin film, for instance, the following four methods are available.

Figure 1:
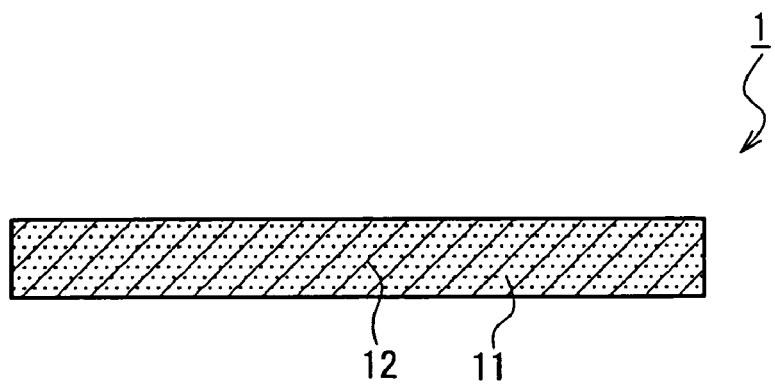
FIG. 1 is a plan view illustrating an example of a medical film of the present invention.

The first method is as follows. First, the gelatin solution is cast in a petri dish as described above, and a reinforcing material is immersed therein so that an internal part of the reinforcing material is impregnated with the gelatin solution. In this case, it is preferable that the reinforcing material is subjected to a hydrophilicity imparting treatment, or that the gelatin solution is deaerated, so that the internal part is impregnated with the gelatin solution sufficiently. Then, the gelatin is caused to gel, and is dried as described above. This causes the gelatin in the reinforcing material to gel as well, concurrently with the formation of a gelatin film, whereby a medical film is prepared in which the reinforcing material and the gelatin film are integrated with each other. More specifically, for example, as shown in the cross-sectional view of FIG. 1, gelatin 11 gels in a reinforcing material 12 so as to be a gelatin film, whereby a single layer laminate is prepared in which the reinforcing material and the gelatin film are integrated with each other. It should be noted that dots in the foregoing drawing schematically represent the gelatin, so as to indicate the presence of the gelling gelatin in the reinforcing material 12, and this applies to FIGS. 2 to 4.

Figure 2A:
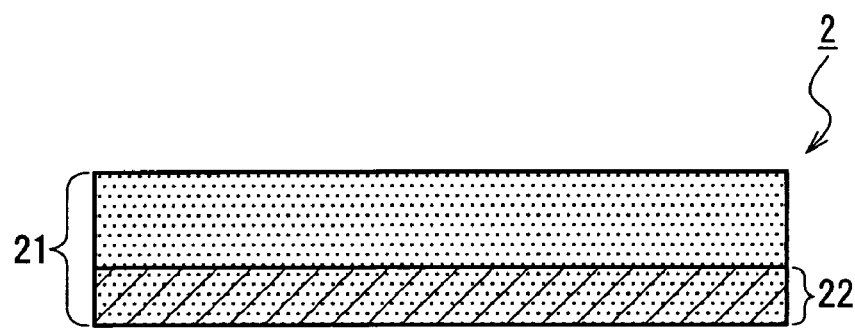
FIGS. 2A and 2B are cross-sectional views illustrating the medical film according to the foregoing example.
Figure 2B:
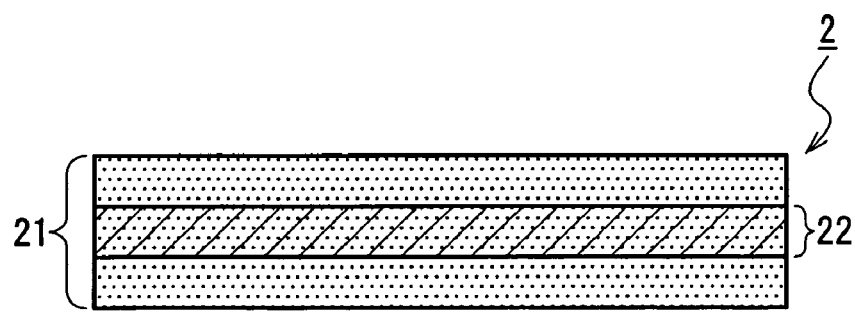

It should be noted that the form of the medical film prepared by the first method may be as shown in the cross-sectional view of FIG. 2A or 2B, for example.

For example, a medical film shown in FIG. 2A has a reinforcing material 22 in an internal part of a gelatin film 21, and the reinforcing material 22 and the gelatin film 21 are integrated due to the gelling of the gelatin that has infiltrated entirely in the reinforcing material 22. In the case of a medical film 2 in such a form, it is possible to make the thickness of the gelatin film 21 (the thickness of the medical film 2) greater than that of the reinforcing material 22 by, for example, adjusting the amount of the gelatin solution or the concentration of gelatin. It also is preferable that, even if the gelatin film that is, for example, in a dried state is thinner than the reinforcing material, the gelatin film is brought into a water-containing state by absorbing moisture when it is used so as to be thicker than the reinforcing material.

Furthermore, for example, in a medical film shown in FIG. 2B, a reinforcing material 22 is embedded entirely in a gelatin film 21, and the reinforcing material 22 and the gelatin film 21 are integrated due to the gelling of the gelatin that has infiltrated entirely in the reinforcing material 22. The medical film in such a form can be prepared by, for example, immersing the reinforcing material in a gelatin solution that has not yet hardened, then supplying the same gelatin solution to the reinforcing material from the above, and allowing the gelatin solution to harden completely. When the reinforcing material is embedded in the gelatin film as described above, both surfaces of the medical film are composed only of the gelatin film. Thus, for example, it is possible to bring the gelatin film alone in the medical film in contact with an entire area of an application site.

Figure 3:
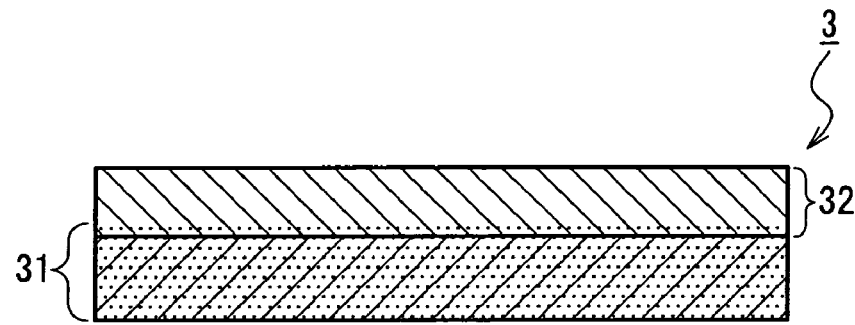
FIG. 3 is a cross-sectional view illustrating another example of a medical film of the present invention.

The second method is as follows. First, the gelatin solution is cast in the petri dish, and the gelatin is caused to start gelling. Then, before the gelatin gels completely, a reinforcing material is placed on the gelatin in a state immediately before gelling. The gelatin is caused to gel completely, and is dried. Since this causes the gelatin solution to infiltrate in the reinforcing material partially, the gelatin gels in the reinforcing material, concurrently with the formation of a gelatin film, whereby a medical film 3 is prepared in which the reinforcing material 32 and the gelatin film 31 are integrated with each other by means of the gelatin in the reinforcing material 32, as shown in the cross-sectional view of FIG. 3. It should be noted that the method for forming the medical film that is in the form as shown in FIG. 3 is not limited to the above-described method. The medical film in such a form also can be prepared by, for example, placing a reinforcing material in a container and then supplying a gelatin solution from above the reinforcing material.

This method does not require, for instance, the deaeration or the like for impregnating the reinforcing material with the gelatin solution sufficiently, and therefore, it enables the integration more easily as compared with the first method.

Figure 4:
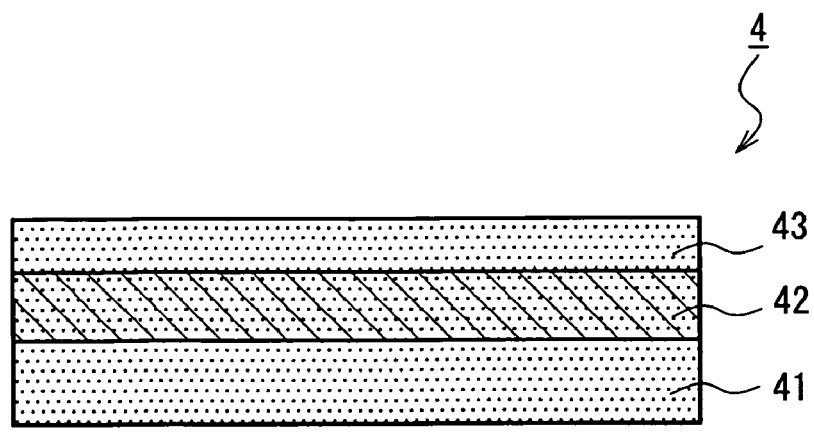
FIG. 4 is a cross-sectional view illustrating still another example of a medical film of the present invention.

The third method is a method in which, for instance, a complex composed of the reinforcing material and the gelatin film that have been prepared in the same manner as in the second method further is immersed in the gelatin solution so that the reinforcing material faces the gelatin solution, and then is dried. This provides a medical film 4 structured so that the reinforcing material 42 is embedded in gelatin films 41 and 43, as shown in FIG. 4. The gelatin solution used for forming the gelatin film 41 and the gelatin solution used for forming the gelatin film 43 have infiltrated in the reinforcing material 42, and the gelatin has hardened inside the reinforcing material 42. It should be noted that in the drawing, the gelatin films 41 and 43 are integrated by means of the gelatin in the reinforcing material 42 due to the second gelling. In the medical film of such a structure, for instance, the reinforcing material is not exposed on a surface thereof. Therefore, it is possible to bring the gelatin film in contact with an entire area of an application site.

The fourth method is as follows. A nonwoven fabric in a desired shape is held between two glass plates that are opposed to each other so that they have a desired thickness beforehand, and the gelatin solution is poured between the glass plates. Then, it is cooled so as to gel, and thereafter, it is dried. In this case also, the gelatin solution infiltrates in the reinforcing material partially, and thereafter gels. As a result, a medical film in which reinforcing material and the gelatin film are integrated with each other can be obtained. Further, since the reinforcing material is not exposed on a surface thereof, as in the medical film obtained by the third method, it is possible, for instance, to bring the gelatin film in contact with an entire area of an application site. Moreover, according to the fourth method, it is possible to make the thickness of the medical film still more uniform.

The foregoing methods utilize the infiltration of the gelatin solution in the reinforcing material so that the gelatin gels also in an entirety or part of an internal part of the reinforcing material. Therefore, the methods allow for sufficient integration of the gelatin film and the reinforcing material, and a medical film thus obtained does not undergo, for instance, the separation of the reinforcing material during use, and is capable of maintaining an excellent strength with respect to the suturing and the like of the medical film. It should be noted that the integration is not limited by the above-described methods, and it may be achieved by, for instance, using an adhesive or the like. Further, after the integration, the above-described cross-linking treatment may be applied.

Further, though the medical film of the present invention, in which the reinforcing material is arranged on the gelatin film as described above, may be used in a sheet form as it is, it alternatively may be formed, for instance, in a cylindrical shape beforehand (this medical film hereinafter referred to as a "cylindrical medical film").

Such a cylindrical medical film can be used, for instance, as an antiadhesive material for a tendon, a nerve, an oviduct, or the like, or an induction tube for a nerve. More specifically, for instance, in a state in which both ends of a cut nerve are inserted in the cylinder of the cylindrical medical film, the nerve and the cylindrical medical film are sutured.

Figure 5:
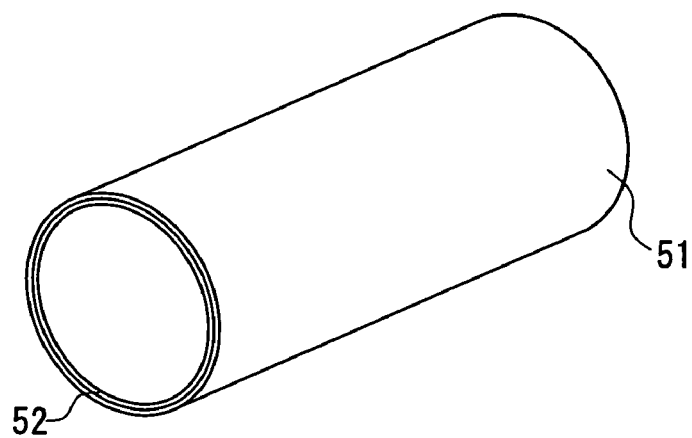
FIG. 5 is a perspective view illustrating still another example of a medical film of the present invention.

The cylindrical medical film has a structure in which, for instance, a gelatin film 51 is arranged on an external surface of a reinforcing material 52 in a cylindrical shape, as shown in the perspective view of FIG. 5. The size thereof is not limited particularly, and can be determined appropriately according to, for instance, an application site. For instance, it has an overall length in a range of 0.3 cm to 30 cm and an inside diameter in a range of 1 mm to 1 cm, and the gelatin film and the reinforcing material have thicknesses as those described above, respectively.

The cylindrical medical film as described above can be prepared, for instance, by the following method. First, a rectangular gelatin film is provided, and then a laminate is prepared by arranging a reinforcing material on one surface of the gelatin film so that the reinforcing material extends over an entire area of the surface of the gelatin film. Then, this is rolled so as to have a cylindrical shape, and the ends in the width direction of the laminate are overlapped and are bonded with an adhesive or sutured with a bioabsorbable suture thread. Thus, a cylindrical medical film is obtained. It should be noted that in the medical film of the present invention, the reinforcing material may be arranged on an internal surface or an external surface of the gelatin film in the cylindrical shape, but considering that the gelatin film provides the adhesion prevention effect, ends of a cut nerve or the like are inserted in the cylinder, and it is necessary to prevent the medical film from adhering to tissues outside, the gelatin film 51 preferably is arranged on an external surface of the reinforcing material 52 as shown in FIG. 5. It should be noted that, for example, a medical film obtained by rolling a gelatin film in which a reinforcing material is embedded as shown in FIG. 2B and FIG. 4 so as to have a cylindrical shape as in FIG. 5 also is preferable, although such is not shown in the drawings. When the medical film has such a structure, all the surfaces thereof are composed of the gelatin film. Accordingly, it is possible to bring the gelatin in contact with an entire area of an application site.

The method for manufacturing the cylindrical medical film is not limited to the above-described manufacturing method. For instance, it may be manufactured by rolling a gelatin film into a cylindrical form and bonding with an adhesive, gelling the gelatin as described above, or the like so as to form a cylindrical body, and thereafter, arranging the reinforcing material on one surface of the gelatin film so that the reinforcing material extends over an entire area of the surface. Alternatively, it can be obtained by placing a gelatin and a reinforcing material in a cylindrical mold, causing the gelatin to gel, and subsequently drying the same.

Figure 6:
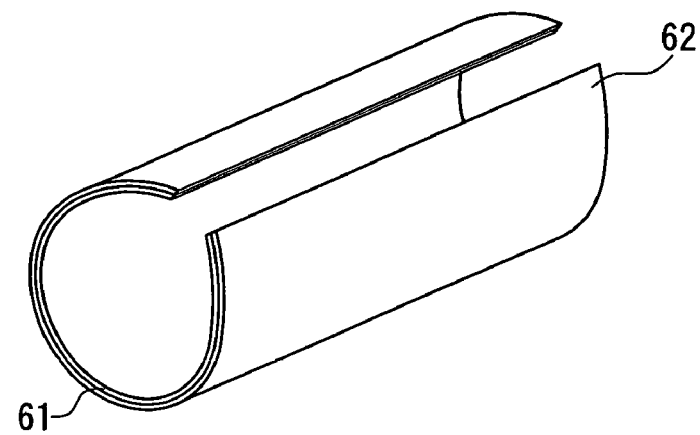
FIG. 6 is a perspective view illustrating still another example of a medical film of the present invention.

Still further, even the medical film in a sheet form as described above also can be used as a cylindrical body when it is used. For instance, as shown in the perspective view of FIG. 6, a medical film in which a reinforcing material 62 is arranged on one surface of a gelatin film 61 so that the reinforcing material 62 extends over an entire area of the surface is rolled, and after a cut tendon or the like is sutured, the medical film is wrapped around the suture portion so as to cover the portion, and is sutured at the overlapping portions. By so doing, it can be used as a cylindrical body.

EXAMPLES

Example 1

Manufacture of Fabric Body

Using a lactic acid-caprolactone copolymer multifilament yarn (thickness: 42 decitex (dtex)), a twin loop knit (thickness: 200 μm) in which a vertical length and a horizontal length of a unit of stitches were both 3.5 mm and a twin loop knit (thickness: 200 μm) in which a vertical length and a horizontal length of a unit of stitches were both 1.5 mm were prepared. The "dtex" (decitex: 1 dtex=1.111×1 denier) is a thickness unit according to the International System of Units (SI). As described above, FIG. 7 illustrates a schematic diagram of a knit stitch structure of a twin loop knit. Each of the twin loop knit fabric bodies was held between two glass plates and subjected to a vacuum heat treatment at 120° C. for 3 hours. Subsequently, each of the heat-treated twin loop knit fabric bodies was subjected to a plasma treatment at room temperature, in oxygen gas at 67 Pa (0.5 torr), with 50 W, for 30 seconds.

Integration with Gelatin Film

Each of the fabric bodies thus obtained was cut into a rectangular shape that was 9 cm long in a lengthwise direction and 7 cm wide in a width direction.

Next, the fabric body (unit of stitches: vertical length 3.5 mm×horizontal length 3.5 mm) thus cut was placed in a petri dish (dimensions: 14 cm×10 cm). A gelatin solution obtained by dissolving gelatin in distilled water so that its concentration became 10 wt % was cast in the petri dish, so that the fabric body was impregnated with the gelatin solution. Then, the fabric body was subjected to air drying as it was, whereby a complex composed of the fabric body and a gelatin film that were integrated with each other was obtained. With regard to this fabric body, three types of complexes different from each other in overall thickness were prepared by casting three different amounts (15 ml, 25 ml, and 35 ml) of the gelatin solution. These three types of complexes had thicknesses, each measured at a portion without the yarn constituting stitches of the fabric body (i.e., measured at a gap portion of stitch loops of the fabric body), of 90 μm, 150 μm, and 210 μm, respectively. Also, with regard to the other fabric body (unit of stitches: vertical length 1.5 mm×horizontal length 1.5 mm), a complex was prepared in the same manner as in the above (in this case, the amount of the gelatin solution was 35 ml). Both surfaces of each of these complexes were subjected to cross-linking by projecting ultraviolet rays thereto using a sterilization lamp (manufactured by Toshiba Corporation, GL-15, wavelength: 254 nm, power of UV lamp: 15 W, irradiation distance: 45 cm) for 10 hours each. In the above-described manner, complexes with a reinforcing material being embedded in a gelatin film were prepared. Note here that the complexes obtained became thicker with an increase in an amount of the gelatin solution used for their preparation.

With regard to each complexes (medical film) obtained in the present example, a tensile strength and a yarn threading tension were measured in the following manner. Furthermore, as Comparative Example 1, three types of films respectively having the above-described thicknesses were prepared by drying and cross-linking the gelatin solution in the same manner as in the above except that no fabric body was provided in the films. With regard to these films, a tensile strength and a yarn threading tension also were measured in the same manner as in the above.

Measurement of the Tensile Strength

Figure 8:
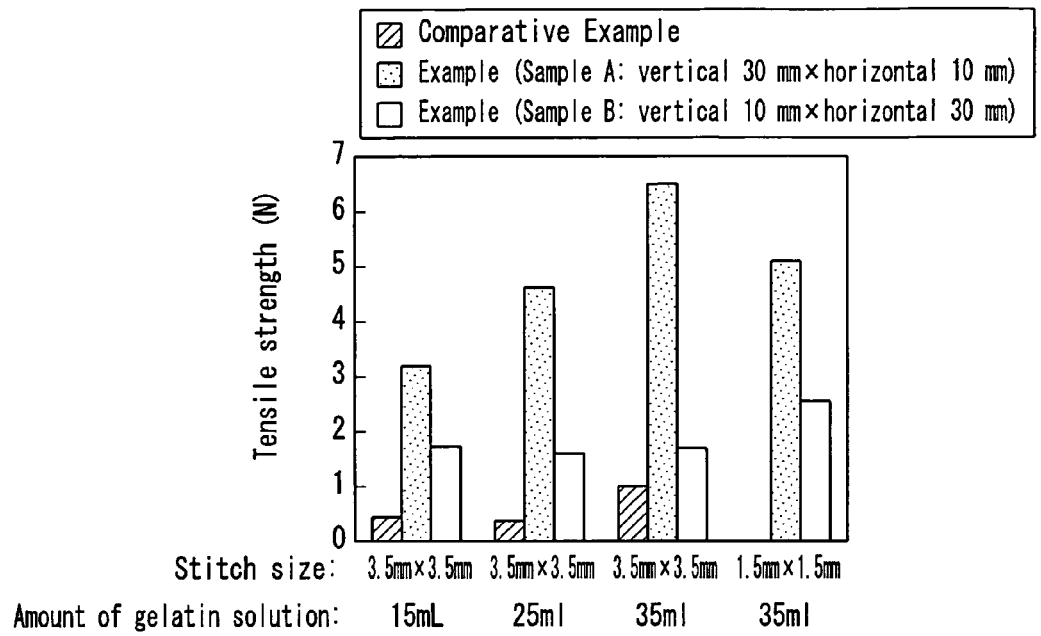
FIG. 8 is a graph showing a tensile strength of a medical film according to an example of the present invention.

Each of the complexes was immersed in a physiological saline solution at 25° C. for 40 minutes. Thereafter, pieces of 10 mm×30 mm were cut out of the complex, and were used as samples. As the samples, the following two types were prepared with regard to each complex: a sample that had been cut out so that a length thereof measured along the vertical direction of stitches of the fabric body was 30 mm and a length thereof measured along the horizontal direction of the same was 10 mm (a sample A); and a sample that had been cut out so that a length thereof measured along the vertical direction of stitches of the fabric body was 10 mm and a length thereof measured along the horizontal direction of the same was 30 mm (a sample B). Then, both ends of each sample in its lengthwise direction were fixed so that a distance between two chucks was 10 mm. Then, each sample was pulled at a rate of 100 mm/min, and the tension at which the sample ruptured was measured using a measuring device (trade name: Instron 4302, manufactured by Instron Corporation). The measurement was carried out five times with regard to each sample, and an average value was determined. Also, these samples were evaluated according to the evaluation criteria shown below. It should be noted that in the case where a sample was evaluated as A or B, it is regarded as sufficiently applicable in practical use. The results are shown in FIG. 8 and Table 1 below. In FIG. 8, the word "vertical" described regarding the sample size means a length measured along the vertical direction of stitches of the fabric body, while the word "horizontal" described regarding the sample size means a length measured along the horizontal direction of stitches of the fabric body.

A: The reinforcing material did not rupture even when the tension was not less than 2 N.
   B: The reinforcing material did not rupture even when the tension was 1 N.
   C: The reinforcing material ruptured when the tension was less than 1 N.

Measurement of the Yarn Threading Tension

Figure 9:
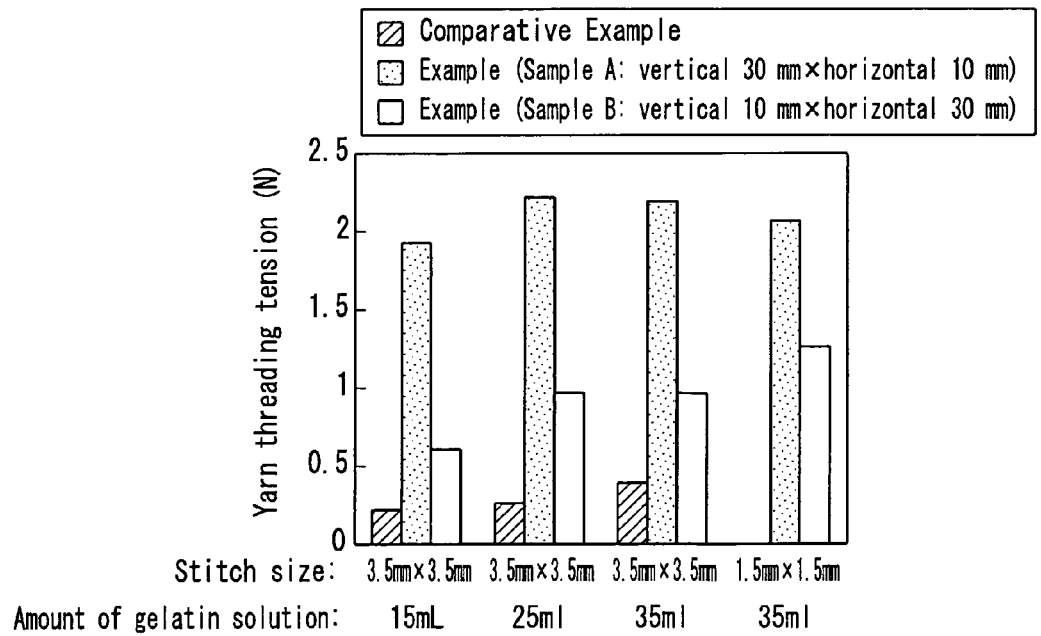
FIG. 9 is a graph showing a yarn threading tension of the medical film according to the foregoing example of the present invention.

Samples were prepared in the same manner as that described in the measurement of the tensile strength above. Then, both ends of each sample in its lengthwise direction were fixed so that a distance between two chucks was 20 mm. Next, a 3-0 nylon suture with needle (Nesco Suture, ½ circle round-bodied needle) (trade name: Nesco Suture, manufactured by AZWELL Inc.) was threaded through the sample at a midpoint in the lengthwise direction and 2 mm from an edge in its width direction, and ends of the suture were fixed at a distance of 50 mm from the point at which the suture was threaded (in a direction perpendicular to the thickness direction of the sample). Then, with the sample being maintained in the fixed state, the ends of the suture were pulled at a rate of 100 mm/min, and a maximal force (yarn threading tension) was measured using a measuring device (trade name: Instron 4302, manufactured by Instron Corporation). The measurement was carried out five times with regard to each sample, and an average value was determined. Also, these samples were evaluated according to the evaluation criteria shown below. It should be noted that in the case where a sample was evaluated as A to C, it is regarded as sufficiently applicable in practical use. The results are shown in FIG. 9 and Table 1 below. In FIG. 9, the word "vertical" described regarding the sample size means a length measured along the vertical direction of stitches of the fabric body, while the word "horizontal" described regarding the sample size means a length measured along the horizontal direction of stitches of the fabric body.

Figure 10A:
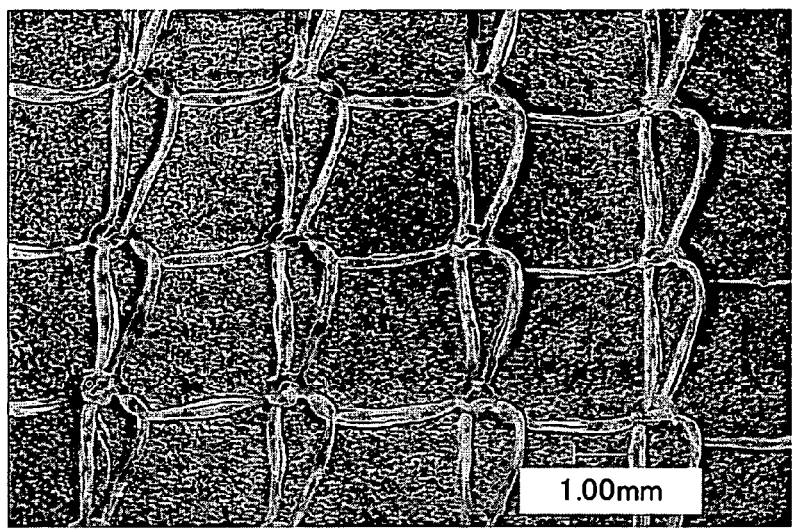
FIG. 10A is a photograph of a twin loop knit and FIGS. 10B and 10C are photographs of warp knitted fabrics.

- A: Neither rupture of the reinforcing material nor exposure of the reinforcing material from the gelatin occurred even when the tension was not less than 2 N.
- B: Neither rupture nor exposure of the reinforcing material occurred even when the tension was not less than 1 N and less than 2 N.
- C: Neither rupture nor exposure of the reinforcing material occurred even when the tension was not less than 0.4 N and less than 1 N.
- C: Rupture of the reinforcing material or exposure of the reinforcing material from the gelatin occurred when the tension was less than 0.4 N.

a vertical length of a unit of stitches was 2.7 mm and a horizontal length of the same was 3.1 mm was prepared. FIG. 10A is a photograph showing a knit stitch structure of the twin knit 2-1 (25× magnification).

(Twin Knit 2-2)

Using a lactic acid-caprolactone copolymer multifilament yarn (thickness: 67 decitex (dtex)), a twin loop knit in which a vertical length of a unit of stitches was 2.7 mm and a horizontal length of the same was 3.1 mm was prepared. A knit stitch structure of the twin knit 2-2 was the same as that shown in FIG. 10A.

(Warp Knitted Fabric 2-3)

Using a lactic acid-caprolactone copolymer multifilament yarn (thickness: 33 decitex (dtex)), a warp knitted fabric (a net with diamond-shaped pores) in which a vertical length of a unit of stitches was 4.2 mm and a horizontal length of the

TABLE 1

|  |  | Stitch size of fabric body (vertical (mm) × horizontal (mm)) | Gelatin solution (ml) | Sample size (vertical (mm) × horizontal (mm)) | Tensile strength | | Yarn threading tension | |
|---|---|---|---|---|---|---|---|---|
|  |  |  |  |  | (N) | Evaluation | (N) | Evaluation |
| Ex. 1 | Sample A | 3.5 × 3.5 | 15 | 30 × 10 | 3.163 | A | 1.926 | B |
|  | Sample A | 3.5 × 3.5 | 25 | 30 × 10 | 4.615 | A | 2.215 | A |
|  | Sample A | 3.5 × 3.5 | 35 | 30 × 10 | 6.467 | A | 2.110 | A |
|  | Sample A | 1.5 × 1.5 | 35 | 30 × 10 | 5.078 | A | 2.073 | A |
|  | Sample B | 3.5 × 3.5 | 15 | 10 × 30 | 1.699 | B | 0.5733 | C |
|  | Sample B | 3.5 × 3.5 | 25 | 10 × 30 | 1.584 | B | 0.9575 | C |
|  | Sample B | 3.5 × 3.5 | 35 | 10 × 30 | 1.699 | B | 0.9526 | C |
|  | Sample B | 1.5 × 1.5 | 35 | 10 × 30 | 2.568 | A | 1.267 | B |
| Comp. Ex. 1 |  | — | 15 | 30 × 10 | 0.4155 | C | 0.2048 | D |
|  |  | — | 25 | 30 × 10 | 0.3636 | C | 0.2372 | D |
|  |  | — | 35 | 30 × 10 | 0.9947 | C | 0.3793 | D |

As can be seen from FIGS. 8 and 9 and Table 1, each complex (medical film) in which the reinforcing material and the gelatin film were integrated with each other exhibited a greater tensile strength and a greater yarn threading tension than those of the gelatin film of Comparative Example 1, which demonstrates that each complex was reinforced sufficiently by the reinforcing material. Moreover, the difference between a tensile strength in the vertical direction and that in the horizontal direction of the complex could be reduced by making stitches of the reinforcing material smaller. This provides an advantage that it is possible to use the medical film without giving consideration to the orientation of the reinforcing material. Furthermore, the strength of the medical film could be improved still further when the gelatin film was made thicker by changing the amount of the gelatin solution.

Example 2

As fabric bodies, complex films were prepared using a twin knit and a warp knitted fabric shown below, respectively, and the strength of the thus-obtained films were determined. Note here that a lactic acid-caprolactone copolymer multifilament yarn used for the preparation of the films was prepared using lactic acid-caprolactone copolymer containing lactide (a dimer of lactic acid) and caprolactone at a composition ratio (a molar ratio) of 75:25 by a known method (see JP 8(1996)-317968 A, for example).

Reinforcing Material (Twin Knit 2-1)

Figure 10B:
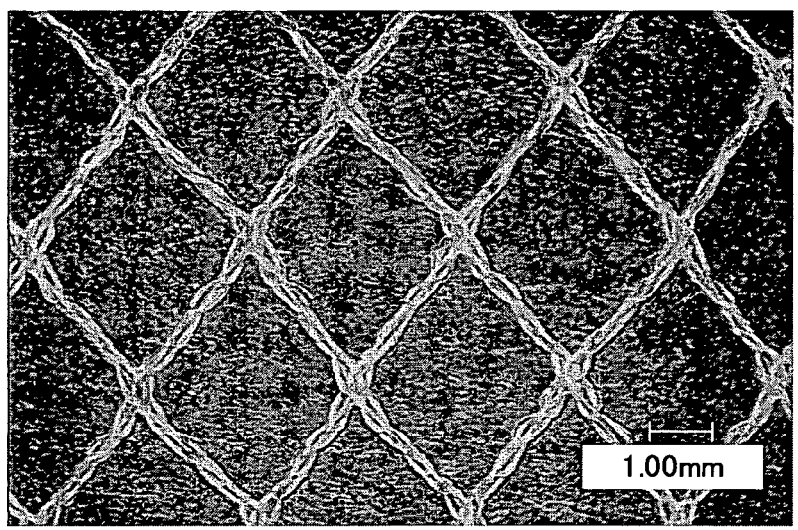

Using a lactic acid-caprolactone copolymer multifilament yarn (thickness: 75 decitex (dtex)), a twin loop knit in which same was 3.9 mm was prepared. FIG. 10B is a photograph showing a knit stitch structure of the warp knitted fabric 2-3 (25× magnification).

(Warp Knitted Fabric 2-4)

Figure 10C:
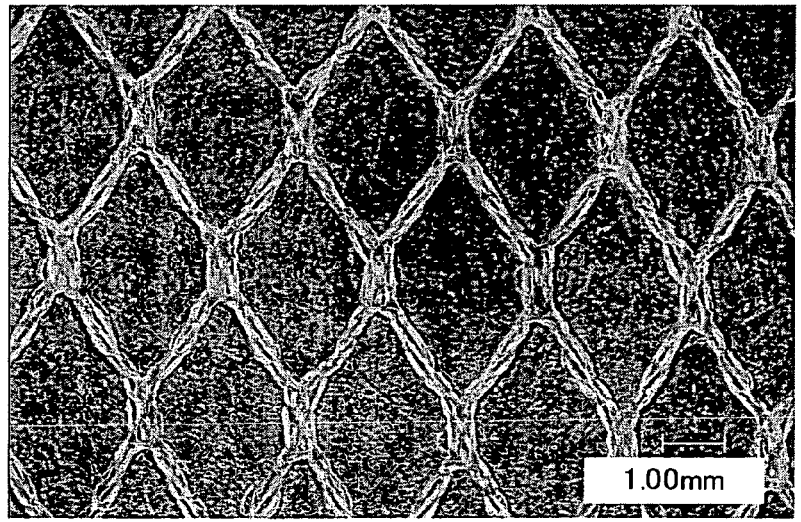

Using a multifilament yarn of the same kind as that used for the preparation of the warp knitted fabric 2-3, a warp knitted fabric (a net with hexagon pores) in which a vertical length of a unit of stitches was 5.1 mm and a horizontal length of the same was 2.7 mm was prepared. FIG. 10C is a photograph showing a knit stitch structure of the warp knitted fabric 2-3 (25× magnification).

Integration with Gelatin Film

The thus-obtained reinforcing material samples (the twin knits 2-1 and 2-2 and the warp knitted fabric 2-3 and 2-4) were subjected to a vacuum heat treatment and a plasma treatment in the same manner as in Example 1. After each of the samples had been placed in a petri dish (dimensions: 13.6 cm×9.6 cm), a gelatin solution obtained by dissolving gelatin in distilled water so that its concentration became 5 wt % was cast in the petri dish, so that the reinforcing material sample was impregnated with the gelatin solution. Then, the sample was subjected to air drying as it was, whereby a complex composed of the reinforcing material sample and the gelatin film that were integrated with each other was obtained. These complexes had thicknesses, each measured at a portion without the yarn constituting stitches of the fabric body (i.e., measured at a gap portion of stitch loops of the fabric body), of about 160 μm. Both surfaces of each of these complexes were subjected to cross-linking by projecting ultraviolet rays thereto using a sterilization lamp (manufactured by Toshiba Corporation, GL-15, wavelength: 254 nm, power of UV lamp: 15 W, irradiation distance: 45 cm) for 10 hours each. In the above-described manner, complexes with a reinforcing material being embedded in a gelatin film were prepared.

Figure 11:
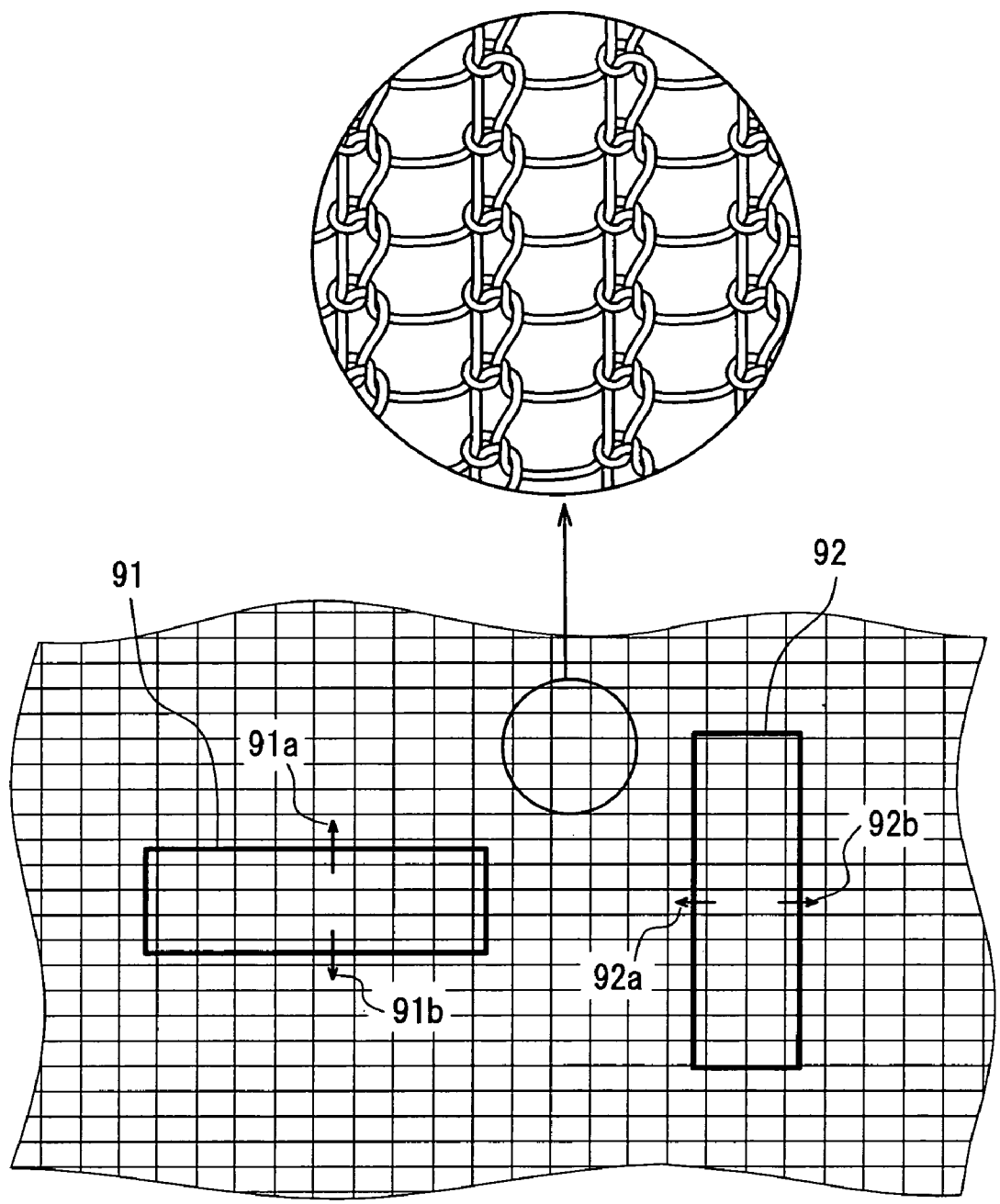
FIG. 11 is a schematic view showing a pattern for cutting out a complex in the foregoing example of the present invention.
Figure 12:
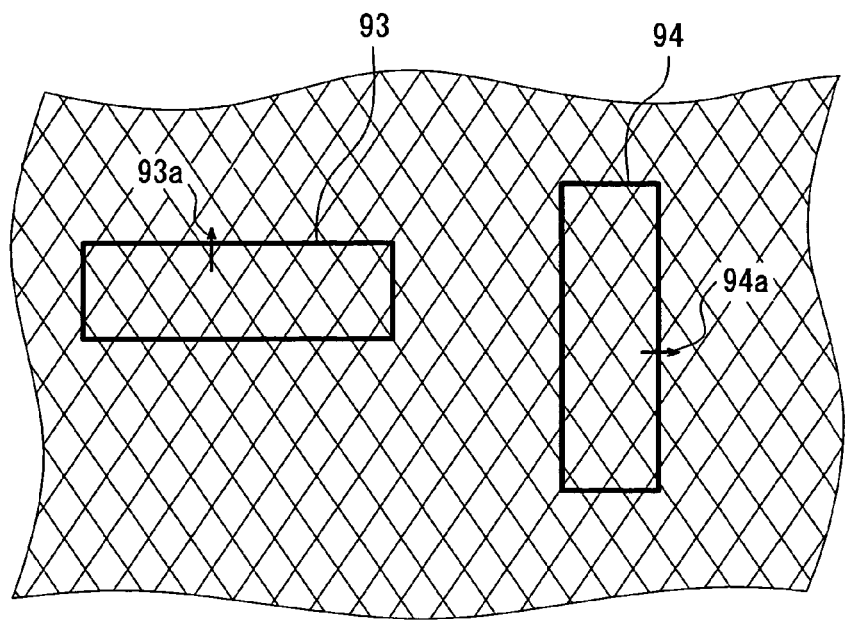
FIG. 12 is a schematic view showing another pattern for cutting out a complex in the foregoing example of the present invention.
Figure 13:
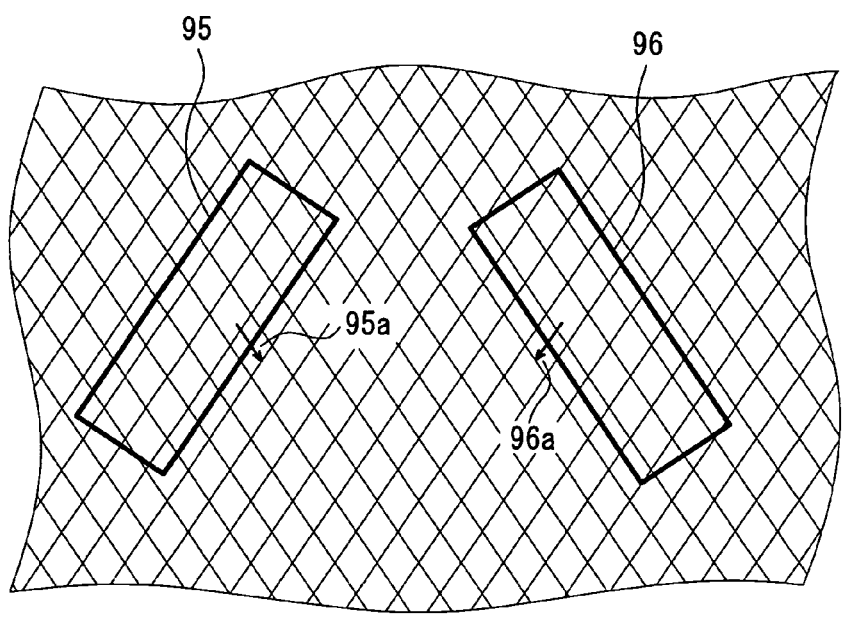
FIG. 13 is a schematic view showing still another pattern for cutting out a complex in the foregoing example of the present invention.

Then, pieces, each having a length of 3 cm and a width of 1 cm, were cut out of each of the complexes thus prepared, and were used as complex samples. FIG. 11 schematically illustrates the directions along which the pieces were cut out of each of the complexes provided with the twin knits, and FIGS. 12 and 13 schematically illustrate the directions along which the pieces were cut out of each of the complexes provided with the warp knitted fabrics. In FIG. 11, the encircled part is an enlarged schematic view showing a knit stitch structure of the twin knit. It should be noted that FIGS. 11 to 13 are intended merely to illustrate the directions along which the pieces were cut out with respect to the stitches so that the size of the pieces, the size of the stitches, the number of the stitches, etc. are not limited to those shown in the drawings. Also, it should be noted that in FIGS. 11 to 13, specific illustration of the knitting pattern is omitted. In FIG. 11, a cut-out piece 91 is referred to as a horizontal-type sample and a cut-out piece 92 is referred to as a vertical-type sample. In FIG. 12, a cut-out piece 93 is referred to as a horizontal-type sample and a cut-out piece 94 is referred to as a vertical-type sample. In FIG. 13, a cut-out piece 95 is referred to as a first diagonal-type sample and a cut-out piece 96 is referred to as a second diagonal-type sample.

With regard to each complex sample (medical film) thus cut out, the tensile strength and the yarn threading tension were measured. They were measured in the same manner as in Example 1 except that each complex was immersed in 10 mM of phosphate buffered saline (PBS: pH 7.4) at 25° C. instead of the physiological saline solution and that, in the measurement of the yarn threading tension, a 5-0 nylon suture with needle (trade name: Nesco Suture, ½ circle round-bodied needle, manufactured by AZWELL Inc.) was used instead of the 3-0 nylon suture with needle. In the measurement of the tensile strength, the nylon suture was threaded through the sample at a midpoint in the lengthwise direction and 2 mm from an edge in its width direction so that it engages with the yarn constituting the reinforcing material. With regard to the horizontal-type sample 91 and the vertical-type sample 92 of the twin knit shown in FIG. 11, the yarn threading tension was measured at both ends in its width direction. The directions in which the suture was pulled with regard to the respective samples are indicated with arrows in FIGS. 11 to 13. More specifically, the threaded suture was pulled in the directions indicated with arrows 91a and 91b with regard to the horizontal-type sample 91 and in the directions indicated with arrows 92a and 92b with regard to the vertical-type sample 92 of the twin knit, as shown in FIG. 11; in the direction indicated with an arrow 93a with regard to the horizontal-type sample 93 and in the direction indicated with an arrow 94a with regard to the vertical-type sample 94 of the warp knitted fabric, as shown in FIG. 12; and in the direction indicated with an arrow 95a with regard to the first diagonal-type sample 95 and in the direction indicated with an arrow 96a with regard to the second diagonal-type sample 96 of the warp knitted fabric, as shown in FIG. 13.

Furthermore, as a reference example, the same test was carried out using a 0.1 mm thick pericardial sheet (trade name: Gore-Tex EPTFE patch II, manufactured by Japan Gore-Tex Inc.). The results are shown in Table 2 below. In Table 2, the word "arrow" in the section of yarn threading tension indicates the direction in which the suture was pulled with regard to each sample shown in FIGS. 11 to 13.

TABLE 2

| | Type of reinforcing material | Complex sample | Tensile strength (N) | Evaluation | Yarn threading tension Arrow | (N) | Evaluation |
|---|---|---|---|---|---|---|---|
| Ex. 2 | Twin knit 2-1 | Horizontal type | 4.91 | A | 91a | 0.98 | C |
| | | | | | 91b | 1.85 | B |
| | | Vertical type | 3.45 | A | 92a | 1.79 | B |
| | | | | | 92b | 3.47 | A |
| | Twin knit 2-2 | Horizontal type | 5.79 | A | 91a | 0.62 | C |
| | | | | | 91b | 1.86 | B |
| | | Vertical type | 2.16 | A | 92a | 2.32 | A |
| | | | | | 92b | 2.59 | A |
| | Warp knitted fabric 2-3 | Horizontal type | 7.62 | A | 93a | 2.13 | A |
| | | Vertical type | 2.25 | A | 94a | 2.76 | A |
| | | 1st diagonal type | 6.67 | A | 95a | 3.84 | A |
| | | 2nd diagonal type | 6.35 | A | 96a | 1.84 | B |
| | Warp knitted fabric 2-4 | Horizontal type | 9.35 | A | 93a | 2.43 | A |
| | | Vertical type | 1.95 | B | 94a | 3.29 | A |
| | | 1st diagonal type | 6.61 | A | 95a | 3.78 | A |
| | | 2nd diagonal type | 7.05 | A | 96a | 2.46 | A |
| Ref. Ex. 1 | | Horizontal type | 22.82 | A | | 3.26 | A |
| | | Vertical type | 23.87 | A | | 3.52 | A |

As can be seen from Table 2, in the case where the twin knits were used as reinforcing materials and also in the case where the warp knitted fabrics were used as reinforcing materials, the complex samples exhibited a sufficient strength. In particular, in the case where the warp knitted fabrics were used as reinforcing materials, each of the complex samples exhibited a considerably excellent yarn threading tension and tensile strength, without causing the yarn of the warp knitted fabric to be raveled out. Especially, in the warp knitted fabric 2-4 (a net with hexagon pores), yarns tangled with one another highly at yarn-intersecting portions of the knit stitch structure. This allowed the warp knitted fabric 2-4 to exhibit a yarn threading tension superior to those of the other reinforcing materials, regardless of the portion where the nylon suture was engaged. Moreover, although the twin knit 2-1, the warp knitted fabric 2-3, and the warp knitted fabric 2-4 had an orientation, they exhibited a yarn threading tension superior to that of the samples of the reference example, depending on the portion where the nylon suture was engaged. Especially, the samples 94 of the warp knitted fabrics 2-3 and 2-4 exhibited considerably excellent yarn threading tensions. Furthermore, each complex of Example 2 exhibited a tensile strength and a yarn threading tension that were considerably superior to those of the samples of Comparative Example 1 shown in Table 1. These results demonstrate that by integrating a reinforcing material with a gelatin film, the obtained medical film can exhibit an excellent strength, and that particularly when a warp knitted fabric is used as a reinforcing material, the obtained medical film can exhibit a considerably excellent strength and thus can serve as a useful medical film.

INDUSTRIAL APPLICABILITY

As specifically described above, the medical film of the present invention can be fixed surely to a predetermined site in a living body, and is capable of preventing usual adhesion of tissues effectively, for example. Furthermore, by forming the medical film in a cylindrical shape, the medical film is useful as an antiadhesive material for a tendon, a nerve, an oviduct, or the like or an induction tube for a nerve or the like, for example. Then, after it finishes performing the function of preventing adhesion etc., it is degraded and absorbed in the living body. Therefore, it does not cause any problem concerning safety.

The invention claimed is:

1. A medical film, comprising:
a gelatin film, and
a reinforcing material made of a biodegradable polymer,
wherein the reinforcing material is a warp knitted fabric,
the warp knitted fabric is in a form of a mesh with diamond-shaped pores or a mesh with hexagon pores,
a unit of stitches of the warp knitted fabric has a vertical length of 0.5 to 8 mm and a horizontal length of 0.5 to 8 mm,
a yarn of the warp knitted fabric includes a multifilament yarn and a thickness of the yarn is in a range of 30 denier to 200 denier (33.3 decitex to 222.2 decitex),
the reinforcing material is disposed on at least one film surface of the gelatin film so as to extend over an entire area in a plane direction,
the reinforcing material is embedded entirely in the gelatin film,
the reinforcing material and the gelatin film are integrated due to gelling of gelatin that has infiltrated entirely in an internal part of the reinforcing material, and
the medical film serves as an antiadhesive material.

2. The medical film according to claim 1, wherein the medical film is in a sheet form or in a cylindrical form.

3. The medical film according to claim 1, wherein the reinforcing material is processed by hot pressing.

4. The medical film according to claim 1, wherein the reinforcing material has a density in a range of 3 g/m² to 200 g/m².

5. The medical film according to claim 1, wherein the reinforcing material has a thickness in a range of 10 μm to 1000 μm.

6. The medical film according to claim 1, wherein the reinforcing material has a yarn threading tension in a range of 0.3 N to 200 N.

7. The medical film according to claim 1, wherein the biodegradable polymer is at least one polymer selected from the group consisting of polylactic acid, lactic acid-caprolactone copolymer, and polyglycolic acid.

8. The medical film according to claim 7, wherein a molar ratio (A:B) of lactide (A) and caprolactone (B) in the lactic acid-caprolactone copolymer is in a range of 85:15 to 40:60.

9. The medical film according to claim 1, wherein the reinforcing material is subjected to a hydrophilicity imparting treatment.

10. The medical film according to claim 9, wherein the hydrophilicity imparting treatment is at least one treatment selected from the group consisting of plasma treatment, glow discharge treatment, corona discharge treatment, ozone treatment, graft treatment, coating, chemical treatment, and ultraviolet irradiation.

11. The medical film according to claim 1, wherein the gelatin film is a cross-linked gelatin film.

12. The medical film according to claim 11, wherein the gelatin film is cross-linked by at least one method selected from the group consisting of ultraviolet treatment, heat treatment, and chemical cross-linking agent treatment.

13. The medical film according to claim 12, wherein the gelatin film is subjected to the ultraviolet treatment and the heat treatment.

14. The medical film according to claim 12, wherein the gelatin film is cross-linked by the ultraviolet treatment under conditions of a power of an ultraviolet lamp of 4 W to 40 W, an irradiation time of 0.1 hour to 100 hours, and an irradiation distance of 5 cm to 100 cm.

15. The medical film according to claim 12, wherein the gelatin film is cross-linked by the ultraviolet treatment under conditions of an ultraviolet intensity of 0.05 mW/cm² to 50 mW/cm² and an ultraviolet dose of 1 J/cm² to 100 J/cm².

16. The medical film according to claim 12, wherein the gelatin film is cross-linked by the heat treatment carried out under vacuum at a temperature of 60° C. to 180° C. for 5 minutes to 72 hours.

17. The medical film according to claim 1, wherein a time of presence of the gelatin film in a living body is in a range of 12 hours to 90 days.

18. The medical film according to claim 1, wherein the gelatin film has a thickness in a range of 20 μm to 2000 μm.

19. The medical film according to claim 1, wherein a concentration of endotoxin contained in the gelatin is not more than 200 EU/g.

20. The medical film according to claim 1, wherein the warp knitted fabric includes yarns formed of a series of intertwining loops.

21. The medical film according to claim 1, wherein yarns of the warp knitted fabric are tangled with one another at yarn-intersecting portions of a knit stitch structure.

22. The medical film according to claim 1, wherein neither rupture nor exposure of the reinforcing material occurs when the tension is less than 1 N.

* * * * *